US011896421B2

United States Patent
Van Heesch et al.

(10) Patent No.: US 11,896,421 B2
(45) Date of Patent: Feb. 13, 2024

(54) MONITORING BLOOD DISTRIBUTION IN A SUBJECT

(71) Applicant: KONINKLIJKE PHILIPS N.V., Eindhoven (NL)

(72) Inventors: Franciscus Hendrikus Van Heesch, Valkenswaard (NL); Nico Maris Adriaan De Wild, Eindhoven (NL); Rick Bezemer, Utrecht (NL); Igor Wilhelmus Franciscus Paulussen, Nuenen (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 591 days.

(21) Appl. No.: 16/967,555

(22) PCT Filed: Feb. 5, 2019

(86) PCT No.: PCT/EP2019/052769
§ 371 (c)(1),
(2) Date: Aug. 5, 2020

(87) PCT Pub. No.: WO2019/154805
PCT Pub. Date: Aug. 15, 2019

(65) Prior Publication Data
US 2021/0085280 A1 Mar. 25, 2021

(30) Foreign Application Priority Data
Feb. 8, 2018 (EP) .................................... 18155683

(51) Int. Cl.
*A61B 8/06* (2006.01)
*A61B 8/08* (2006.01)

(52) U.S. Cl.
CPC ............... *A61B 8/06* (2013.01); *A61B 8/488* (2013.01)

(58) Field of Classification Search
CPC ................................. A61B 8/06; A61B 8/488
See application file for complete search history.

(56) References Cited

U.S. PATENT DOCUMENTS

| 4,424,814 A | 1/1984 | Secunda |
| 5,997,479 A | 12/1999 | Savord |

(Continued)

FOREIGN PATENT DOCUMENTS

| AU | 2015346054 B2 * | 4/2020 | ........... A61B 5/0002 |
| WO | 2013005179 A1 | 1/2013 | |

(Continued)

OTHER PUBLICATIONS

Schiffner, Rene et al "Redistribution of Cerebral Blood Flow during Severe Hypovolemia and Reperfusion in a Sheep Model: Critical Role of 1-Adrenergic Signaling", International Journal of Molecular Sciences, vol. 18, No. 1031, 2017, pp. 1-15.

Arbeille, Philippe "Doppler Sensors and Harnesses for Cardiac and Peripheral Arterial Flow Monitoring", Ultrasound in Medicine and Biology, vol. 23, No. 3, 1997.

(Continued)

*Primary Examiner* — Boniface Ngathi

(57) ABSTRACT

A system for monitoring blood distribution in a subject, the system comprising a processor(38) responsive to Doppler ultrasound data representing arterial blood flow in at least two different locations of the subject, such as the neck and the arm, to obtain velocity (C, B1, B2, B3) or volumetric flow rate at each location, to monitor changes in a predetermined function of the blood flows, and to provide an output indicative of the monitored changes which may result from blood volume centralization. This can indicate the onset of hypovolemia or hypervolemia.

18 Claims, 8 Drawing Sheets

(56) References Cited

U.S. PATENT DOCUMENTS

| | | | |
|---|---|---|---|
| 6,013,032 | A | 1/2000 | Savord |
| 6,283,919 | B1 | 9/2001 | Roundhill |
| 6,443,896 | B1 | 9/2002 | Detmer |
| 6,458,083 | B1 | 10/2002 | Jago |
| 6,530,885 | B1 | 3/2003 | Entrekin |
| 6,623,432 | B2 | 9/2003 | Powers |
| 2004/0243006 | A1 | 12/2004 | Nakata et al. |
| 2010/0081942 | A1 * | 4/2010 | Huiku .................... G16H 40/60 600/483 |
| 2010/0121192 | A1 * | 5/2010 | Nogata ................. A61B 8/483 600/443 |
| 2010/0312115 | A1 | 12/2010 | Dentinger |
| 2011/0137173 | A1 | 6/2011 | Lowe |
| 2013/0303916 | A1 | 11/2013 | Aoki et al. |

FOREIGN PATENT DOCUMENTS

| | | | |
|---|---|---|---|
| WO | 2013110929 A1 | 8/2013 | |
| WO | 2016077765 A1 | 5/2016 | |
| WO | WO-2017093150 A1 * | 6/2017 | |
| WO | WO-2017096487 A1 * | 6/2017 | ............. A61B 5/026 |
| WO | WO-2017109080 A1 * | 6/2017 | ............... A61B 8/06 |

OTHER PUBLICATIONS

Maixner, William et al. "Early Detection of Hypovolemia From Directional Arterial Flow Velocity", Circulatory Shock, vol. 5, pp. 35-41, 1978.

International Search Report and Written Opinion of PCT/EP2019/052769, dated Mar. 25, 2019.

\* cited by examiner

MONITORING BLOOD DISTRIBUTION IN A SUBJECT

This application is the U.S. National Phase application under 35 U.S.C. § 371 of International Application No. PCT/EP2019/052769, filed on Feb. 5, 2019, which claims the benefit of European Application Serial No. 18155683.8, filed Feb. 8, 2018. These applications are hereby incorporated by reference herein.

FIELD OF THE INVENTION

The present invention relates to a system and a method for monitoring blood distribution in a subject, for detecting hypovolemia and to a method of processing data to detect hypovolemia in a patient.

The present invention further relates to a computer program product for implementing such a method.

BACKGROUND OF THE INVENTION

Hypovolemia, a state of decreased blood volume, especially blood plasma, can be caused by bleeding and is a common complication in critical care. An important physiological response to this is haemodynamic centralization; i.e. redistribution of blood volume from the limbs to the thorax and head. The body does this by peripheral vasoconstriction, limiting the inflow of blood into the limbs, which initially enables the heart to maintain its generation of an adequate blood pressure for the central, vital organs. When hypovolemia progresses, the body cannot compensate anymore and it will become unstable. Blood pressure will drop, leading to hypoperfusion of vital organs.

At the organ level, the body is able to maintain perfusion under a range of blood pressures, i.e. by autoregulation. For some organs, such as the brain, adequate perfusion can be maintained from relatively low to relatively high blood pressures. For other organs or body parts, such as the limbs and kidneys, perfusion is only maintained well within a small blood pressure range—outside that range the perfusion is directly dependent on the blood pressure. This is illustrated in FIG. 1, showing volumetric blood flow through an organ as a function of blood pressure and indicating volume status. The diameter of the blood vessel is taken into account for each graph. Line 10 represents the flow through the carotid artery towards the brain and line 12 represents the flow through the brachial artery. The status p1 is hypovolemia, p2 is normovolemia and p3 is hypervolemia. When the blood pressure declines from p2 to p1, centralization occurs and brachial flow 12 is strongly affected, shown by the slope in this region. Carotid flow 10 is largely unaffected until the volume declines still further, shown by the slope in this region. Hence, in case of centralization from hypovolemia, the flow to a low-priority organ or limb will be significantly reduced, and dependent on blood pressure, while flow to a high-priority organ such as the brain will be maintained and will be largely independent of blood pressure.

As blood pressure is initially maintained by centralization, conventional measurements such as arterial blood pressure and heart rate are unable to identify the onset and early phase of volume loss leading to hypovolemia. Hence, it would be desirable that centralization could be detected earlier, to allow timely intervention i.e. finding the cause and providing supportive fluid management.

There is therefore a need for a way of detecting early the onset of hypovolemia in a subject.

SUMMARY OF THE INVENTION

The invention is defined in the claims.

The present invention provides a system for monitoring blood distribution in a subject, the system comprising:
an input for receiving Doppler ultrasound data representing arterial blood flow in at least two different locations of the subject;
a processor adapted to:
determine a predetermined function of the arterial blood flows at the locations; and
monitor changes in the predetermined function; and
an output for providing blood distribution information based on the monitored changes.

Since the blood flow varies with centralization differently in the vascular system depending upon the distance from the heart, the invention can detect haemodynamic centralization and therefore the onset of hypovolemia, and it can detect hypervolemia in a similar way, based on these differences.

Many different measures of blood flow can be used to monitor differential changes taking place at two different locations. Averages can be taken over a selected period of time, of flow velocity or of volumetric flow rate. This can reduce the effect of noise and of insignificant fluctuations, and can provide a common basis for the comparison of the flows. The measure of the blood flow may comprise the flow velocity integrated over the period of a heart beat of the subject. Flow velocity varies cyclically, and its integration over a heart beat can provide a suitable average value of flow.

The processor is preferably responsive to a measure of the diameter of the artery at each location at which the Doppler ultrasound data representing arterial blood flow velocity are obtained, and the measure of the blood flow preferably then comprises the volumetric rate of flow based on the diameter and the flow velocity. The diameter can for example be measured by pulse wave ultrasound Doppler techniques. Where ultrasound probes (patches) are used on the subject to obtain the blood flow data, one of these probes, or a different probe, can be driven to provide the image of the arterial wall that can be used to derive the diameter, using known techniques. However, arterial diameter can be obtained in other ways, such as based on the height, weight, age, gender, etc. of the patient from medical records.

The arterial blood flow preferably comprises the volumetric flow rate integrated over the period of a heart beat of the subject.

The predetermined function of the arterial blood flows is preferably their numerical ratio. This could for example be the ratio of the blood flow velocities, or of their time-integrated values, or of the volumetric blood flows or of the time-integrated volumetric blood flows, taken from probes at the different locations. However, other mathematical functions could be used instead of numerical division. For example a constant could be added to or subtracted from each flow value before the division process, or quadratic or more complex functions could be applied to determine when the status has departed from normovolemia. Look-up tables could be used instead of mathematical functions in computations.

The processor is preferably configured to compare the predetermined function with a predetermined range of values of that function, and to provide an output indicative of the outcome of that comparison as an indication of potential or early hypovolemia or hypervolemia in the subject. For example, the numerical ratio can be compared with upper and lower values of a range, or with a specific normal value. High values of the ratio between carotid arterial flow and brachial arterial flow indicate hypovolemia, and low values indicate hypervolemia.

The system may comprise a fluid management system, for example linked to the processor wirelessly or by cable within a hospital network, configured to provide fluid to the subject and responsive to the output from the processor indicative of potential hypovolemia or hypervolemia in the subject to control the provision of fluid. In this way, the recognition that the subject may have the onset of hypovolemia can be used to provide fluid, e.g. through an intravenous drip, to treat the condition.

The processor may conveniently be configured also to provide an output indicative of the cardiac output of the subject, based on blood perfusion at at least one of the locations obtained by integrating over time the blood flow velocity at that location multiplied by the diameter of the artery at that location, obtained from an input to the processor. This could provide a display of a number of haemodynamic indications and/or vital signs such as blood pressure and pulse.

The system may comprise at least two Doppler ultrasound probes configured to measure the arterial blood flow velocity in the at least two different locations of the subject and to provide the Doppler ultrasound data to the processor. These may for example be provided as a kit, and they are preferably connectable by cable to the processor. The driving of the probes in transmission and reception cycles can be controlled locally at the probe or in the processor or another part of the overall system.

The system may comprise at least one Doppler ultrasound probe configured to image the artery at one of the locations of the subject to provide to the processor a measure of the diameter of the artery. It may be operated using pulse wave Doppler technology. This also may have its own local drive arrangement, or it may be driven by the processor or another part of the overall system.

The system may comprise a subject monitor configured to display haemodynamic data of the subject including the output indicative of the monitored changes.

The invention also provides a method of monitoring blood distribution in a subject, comprising:

receiving Doppler ultrasound data representing arterial blood flow in at least two different locations of the subject;
determining a predetermined function of the arterial blood flows at the locations;
monitoring changes in the predetermined function; and
providing blood distribution information based on the monitored changes.

This preferably comprises comparing the predetermined function with a predetermined range of values of that function, and providing an output indicative of the outcome of that comparison as an indication of potential hypovolemia or hypervolemia in the subject.

The two locations of the subject are preferably at substantially different distances from the heart, preferably at the carotid artery and at a brachial, femoral or radial artery. This provides information on blood flow which can detect the centralization characteristic of hypovolemia, since flow is initially affected more in the peripheral regions of the body than it is closer to the heart.

The invention also provides a computer program product comprising a computer readable storage medium having computer readable program instructions embodied therewith for, when executed on a data processor of the processor of the system described above, cause the system to implement the method described above. Such a computer program product may be used to configure existing patient monitoring systems to implement the embodiments of the present invention, thereby avoiding the need for such existing patient monitoring systems to be replaced. As such, the availability of such a computer program product is a cost-effective manner of implementing the embodiments of the present invention. The invention can use conventional ultrasound probes or a low profile ultrasound probe (patch) suitable to be coupled to the body for a longer period of time.

BRIEF DESCRIPTION OF THE DRAWINGS

Embodiments of the invention are described in more detail and by way of non-limiting examples with reference to the accompanying drawings, wherein.

DETAILED DESCRIPTION OF THE EMBODIMENTS

Figure 1:
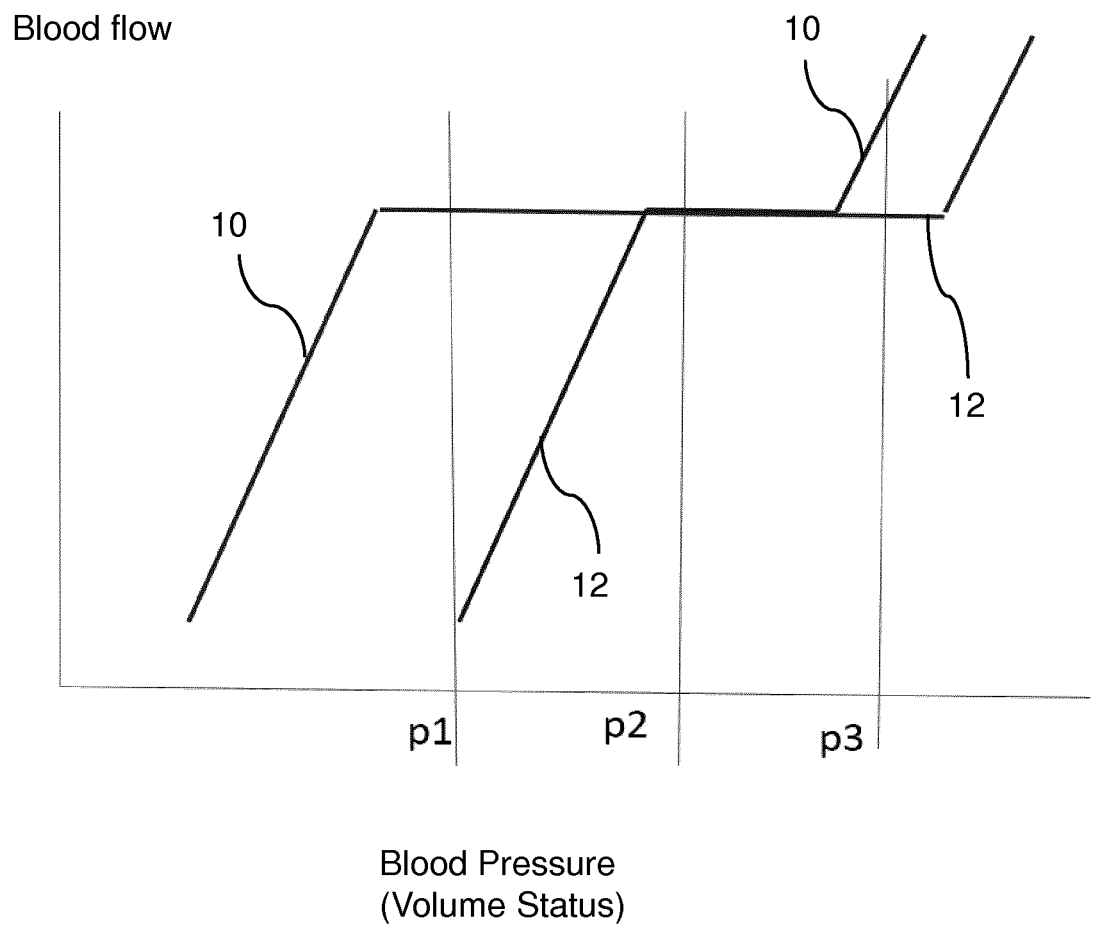
FIG. 1 is a graph of blood pressure and blood flow for two different parts of the body.

It should be understood that the Figures are merely schematic and are not drawn to scale. It should also be understood that the same reference numerals are used throughout the Figures to indicate the same or similar parts.

The invention uses Doppler data from two different ultrasonic probes placed at different locations on the body of the subject, preferably superficially and fixed using patches, to detect the onset of hypovolemia or hypervolemia from changes in the data, preferably in the ratio of measures of arterial blood flow at those locations. Since the blood flow velocity and the volumetric blood flow rate both vary differently (see FIG. 1) when centralization occurs depending upon their proximity to the heart, this difference is exploited to provide a warning that centralization is occurring, and thus that the subject may be suffering from hypovolemia.

This can then lead to immediate treatment such as appropriate fluid management, which can be provided manually or automatically. For hypovolemia, fluids would be needed to compensate for blood plasma loss, and for hypervolemia diuretics could be used for example.

An overall system for use in a hospital will first be described. This comprises the ultrasonic probes and a controller connected to a monitor for displaying the haemodynamic information for the subject, including the status of the blood flow ratio.

The continuously shrinking form factor of ultrasound devices means that such devices can now be deployed as wearable sensors, e.g. patches, such as for the sake of (semi-) continuous patient monitoring in a clinical setting such as hospital or another medical facility. As is well-known per se, ultrasound devices may be used to collect haemodynamic data through the use of Doppler ultrasound, such as blood flow including peak flow, velocity and vascular diameter from which patient parameters such as arterial perfusion, circulatory volume status, fluid responsiveness, haemodynamic stability and so on may be derived. It for example may be useful to monitor such haemodynamic parameters in haemodynamically unstable patients, e.g. patients recovering from surgery.

Typically, such monitoring results are displayed on a patient monitor, i.e. a display device displaying one or more of such parameters on its display screen, where the parameters may be displayed as traces that progress in time across a dedicated display area such that a caregiver can evaluate the haemodynamic stability of the patient by evaluating the displayed traces. In addition, the patient monitor typically comprises a controller that evaluates the haemodynamic data in order to generate an alarm upon detecting an anomaly in the haemodynamic data, such that a caregiver can be alerted and provide any medical attention the patient may need.

This is for instance known from US 2010/0312115 A1, which discloses a method for continuous non-invasive haemodynamic state monitoring in a subject by acquiring continuous ultrasound data via an ultrasound transducer attached to the subject. Continuous arterial waveforms are estimated based upon the acquired ultrasound data and haemodynamic parameters are derived for each cardiac cycle from the arterial waveforms. A current haemodynamic state of the subject is defined by setting limits on one or more haemodynamic parameters based upon the variation of these parameters over an initial period of time, which are used to continuously monitor a haemodynamic state of the subject by comparing a current state for one or more haemodynamic parameters of the subject to previously determined limits for the one or more haemodynamic parameters. A trigger signal or alarm is output to a haemodynamic state monitor in an event that a change is detected in the current state of the one or more haemodynamic parameters, or else the arterial parameters are converted into a continuous estimate of the arterial blood pressure in an event that a change is not detected.

When deploying a wearable ultrasound device onto the patient for such monitoring, the ultrasound device is typically configurable in order to find a patient's artery for monitoring and/or optimizing the signal to noise ratio of the ultrasound echo signals acquired with the ultrasound device. For example, the ultrasound device may comprise a plurality of ultrasound transducers that may be individually addressed in a configurable manner in order to electronically steer, i.e. vary the angle of, the ultrasound beam produced by the ultrasound device in order to locate the patient's artery in the field of view of the ultrasound device. This may involve manual positioning of the ultrasound device onto the patient followed by electronic configuration of the ultrasound device to obtain the optimal configuration of the ultrasound device in terms of the aforementioned signal to noise ratio of its acquired echo signals.

Figure 2:
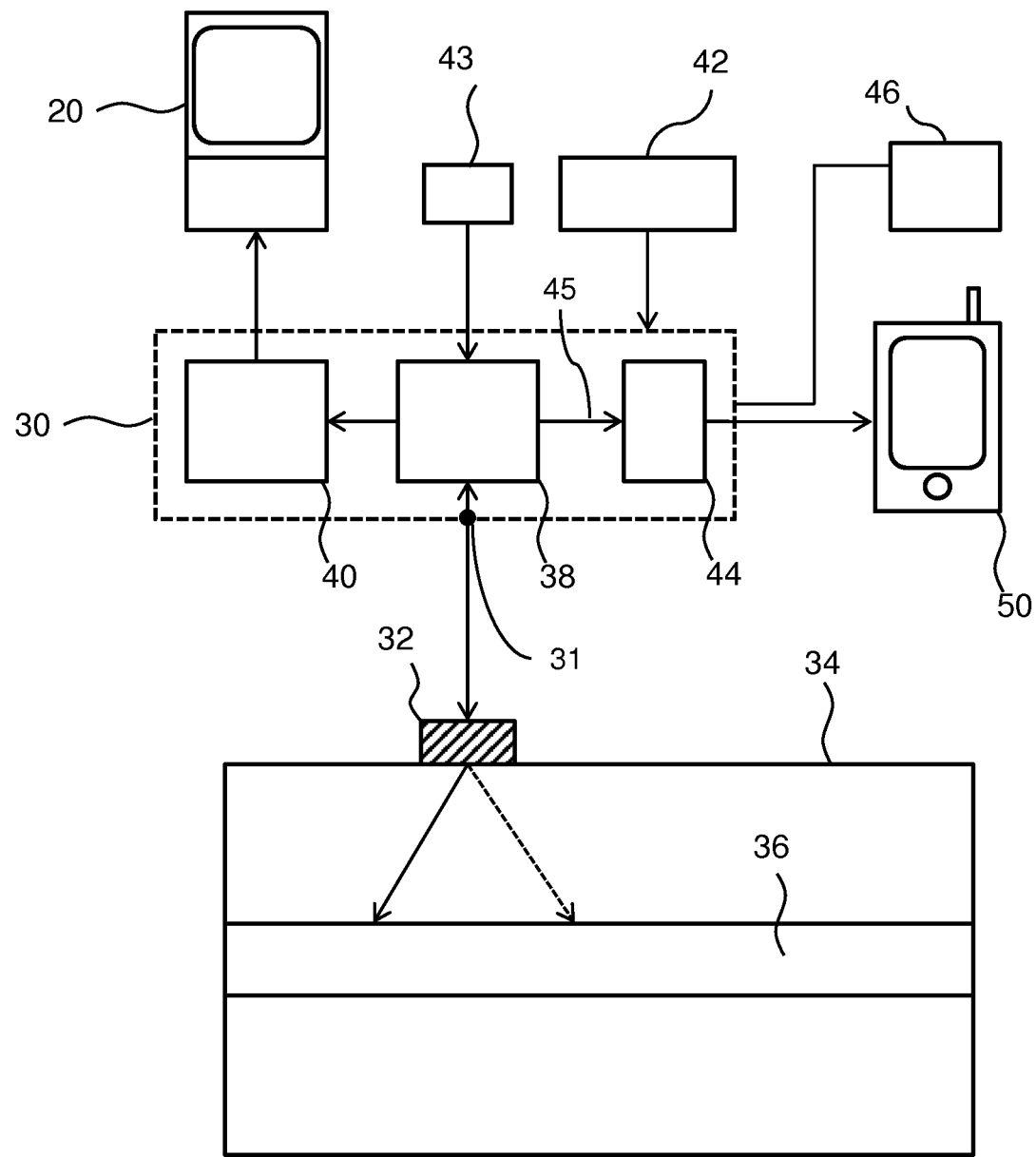
FIG. 2 schematically depicts a patient monitoring system that may incorporate the invention.

FIG. 2 schematically depicts a patient monitoring system 14 which, although only one probe is shown, may embody the present invention using two or more probes. The patient monitoring system 14 comprises a patient monitor 20 under control of a patient monitor controller 30. The patient monitor controller 30 is adapted to receive ultrasound signals, e.g. ultrasound Doppler signals, at an input 31 connected to a wearable ultrasound sensor probe 32 positioned on a body portion 34 such as an arm or a leg, or the neck, of a patient in order to monitor an artery 36 within the body portion 34. More particularly, the wearable ultrasound sensor probe 32 typically is arranged to obtain a series of ultrasound measurements from which the patient monitor controller 30 can derive haemodynamic (hemodynamic) data pertaining to the blood flow through the artery 36 of the patient and control the patient monitor 20 to display the derived haemodynamic data on the display screen of the patient monitor 20.

The patient monitor controller 30 typically comprises a processor arrangement including one or more processors, here depicted by way of non-limiting example by a processor 38 that receives the ultrasound measurement data from the wearable ultrasound sensor probe 32 and processes the received ultrasound measurement data to obtain the haemodynamic data to be displayed on the patient monitor 20 and optionally to perform evaluations of the obtained haemodynamic data such as to determine trends in the haemodynamic data over time such as a variance in the haemodynamic data across a series of ultrasound measurements received from the wearable ultrasound sensor probe 32. In the context of the present application, where reference is made to a series of ultrasound measurements it should be understood that this refers to a plurality of measurements performed during one or more cardiac cycles of the patient from which the haemodynamic data pertaining to these cardiac cycles can be derived. Preferably, the ultrasound measurements comprise ultrasound Doppler measurements from which such haemodynamic data can be derived. The processor arrangement as shown in FIG. 2 further comprises a synchronization unit 40 that synchronizes between the processor 38 and the patient monitor 20, for example to avoid a reconfiguration of the wearable ultrasound sensor probe 32 causing a disruption of the continuity of the haemodynamic data displayed on the patient monitor 20. Although the processor 38 and the synchronization unit 40 are shown as separate entities, it will be immediately apparent to the skilled person that such units may be realized by a single processor or a plurality of processors working together, e.g. separate processors or discrete processor cores of a single multi-core processor.

The patient monitor controller 30 may be responsive to a user interface 42, which may take any suitable form. For example, the user interface 42 may be a touchscreen of the patient monitor 20 or of a separate device that is communicatively coupled to the patient monitor controller 30 in a wired or wireless fashion. Alternatively, the user interface 42 may take the form of a touchpad, keyboard, mouse, trackball and so on or combinations thereof as will be immediately apparent to the skilled person. The user interface 42 may be used by a user of the patient monitoring system 14 to configure which haemodynamic data is to be displayed on the display screen of the patient monitor 20. For example, the user may select one or more haemodynamic waveforms such as (beat-to-beat variability in) flow or peak flow, velocity and vascular diameter (PFV, PVV and VDV) and derived parameters such as arterial perfusion, circulatory volume status, fluid responsiveness and haemodynamic status to be displayed on the patient monitor 20, potentially together with an ultrasound image of the patient's artery as captured by the wearable ultrasound sensor probe 32.

The patient monitor controller 30 may be responsive to a further patient monitoring device 43 such as a ventilator, an ECG monitoring device and so on from which the patient monitor controller 30 receives further vital signs information of the patient being monitored with the wearable ultrasound sensor probe 32. As will be readily understood by the skilled person, the user of the patient monitoring system 14 may configure the system to also display such further vital signs information onto the patient monitor 20, e.g. through the user interface 42.

The patient monitor controller 30 may further comprise an alarm generation unit 44 for generating an alarm when the processor 38 detects an anomaly in the haemodynamic data derived from the series of ultrasound measurements received from the wearable ultrasound sensor probe 32. Such an alarm generation unit 44 receives an output 45 from the computing unit and it may take any suitable form such as that of a loudspeaker or the like for generating an audible alarm, a communication module for transmitting the alarm to a remote device 50 such as a pager, smart phone or the like in order to alert a caregiver to the fact that such an anomaly has been detected. Such a communication module may be a wireless communication module implementing any suitable wireless communication standard such as Wi-Fi (Registered Trade Mark), Bluetooth (Registered Trade Mark), a mobile communication standard such as GSM or UMTS, and so on. Alternatively, the communication module may be a wired communication module that relays the alarm signal to a remote device 50 over a wired network using any suitable communication protocol. The alarm generation unit 44 in yet another embodiment is adapted to generate both an audible alarm as well as alarm signal for the remote device 50.

The controller 30 may compare the inputs from the different monitoring sources 32, 43 to determine whether there is an actual physiological change in the patient such that the alarm generation unit 44 of the patient monitor controller 30 may generate the aforementioned alarm to attract the attention of a caregiver such that the patient can receive the necessary medical attention.

The controller 30 in this example provides an output signal to a fluid management system 46 such as a bedside intravenous drip control, to set the fluid dispense rate based on the monitored status of the patient.

The wearable ultrasound sensor probe 32 may comprise a plurality of ultrasound transducers such as piezoelectric transducers or preferably capacitive micro-machined ultrasound transducers (CMUTs), which may be individually addressable in order to configure the operation of the wearable ultrasound sensor probe 32. For example, the individual addressing of the ultrasound transducers may be controlled to configure the beam angle of the ultrasound beam produced with the wearable ultrasound sensor probe 32 as indicated by the solid and dashed arrows emanating from the wearable ultrasound sensor probe 32 in FIG. 2. Such configuration of the wearable ultrasound sensor 32 may be used to bring the artery 36 of the patient in the field of view of the wearable ultrasound sensor probe 32 after placement of the wearable ultrasound sensor probe 32 on the body region 34 of the patient. The wearable ultrasound sensor probe 32 may come in any suitable form, such as an adhesive patch, a sensor that is strapped to the body portion 34 or a combination thereof. Other suitable embodiments of the wearable ultrasound sensor probe 32 for securing it to the body region 34 of the patient will be immediately apparent to the skilled person. The wearable ultrasound sensor probe 32 may comprise a configuration unit (not shown) responsive to the synchronization unit 40 of the patient monitor controller 30, which configuration unit may be adapted to configure the wearable ultrasound sensor. Alternatively, the processor arrangement of the patient monitor controller 30, e.g. the processor 38 and/or the synchronization unit 40 may be adapted to configure the wearable ultrasound sensor probe 32 as will be explained in more detail below.

The positioning and calibration of the wearable ultrasound sensor probe 32 will be explained in further detail with the aid of FIG. 3, which depicts a flowchart of a positioning and calibration method of the wearable ultrasound sensor probe 32, here a 2-D ultrasound sensor. The method commences in operation 61 with the provision of the wearable ultrasound sensor probe 32 after which the method proceeds to operation 63 in which the wearable ultrasound sensor probe 32 is manually positioned onto the body region of the patient by the caregiver and the wearable ultrasound sensor probe 32 is electronically calibrated, e.g. by systematic variation of the beam angle generated by the wearable ultrasound sensor probe 32 in order to detect an artery 36 of the patient in the Doppler ultrasound data generated with the wearable ultrasound sensor probe 32. It is checked in operation 65 if such an artery 36 can be detected. If such an artery 36 cannot be detected, the method returns to operation 63 in which the caregiver manually repositions the wearable ultrasound sensor probe 32 after which its electronic calibration is repeated until the artery 36 is found after which the method proceeds to operation 67.

In operation 67, a region of interest close to the artery 36 is selected and in operation 69 a biplane view of the artery is generated to check alignment of the wearable ultrasound sensor probe 32 with the artery 36. In operation 71, the respective diameters of the artery 36 are evaluated systematically during manual repositioning, in operation 73, of the wearable ultrasound sensor probe 32 by the caregiver, optionally aided by acoustic guidance signals generated by the alarm generating unit 44. This iterative process in operations 71 and 73 is repeated until the maximum diameter of the artery 36 in both view planes is obtained, which is indicative of the optimal alignment of the wearable ultrasound sensor probe 32 with the artery 36. Upon achieving such an optimal alignment, which is the positive outcome of the evaluation operation 71, the method terminates in operation 75.

Figure 3:
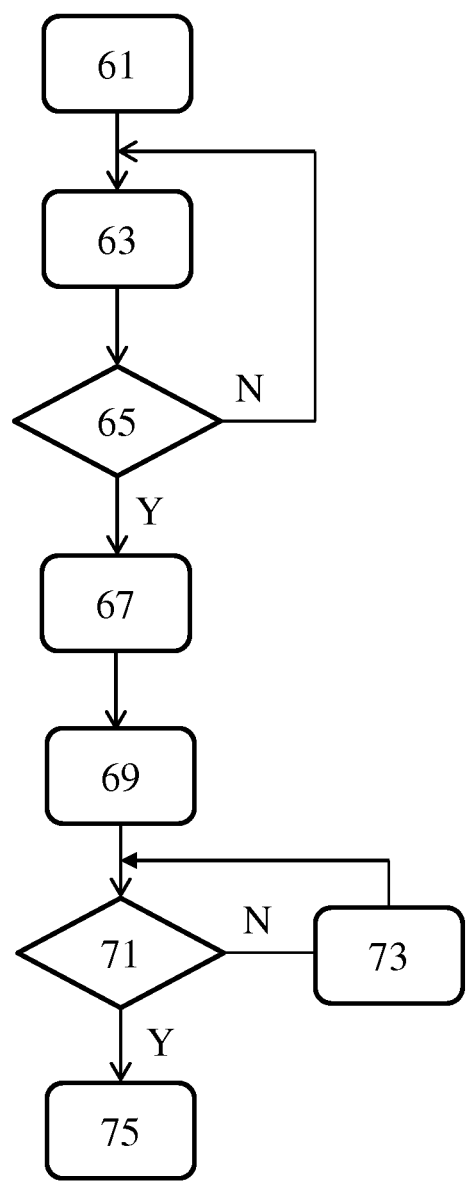
FIG. 3 is a flowchart of a configuration method for a 2-D or 3-D ultrasound patch.

The positioning and calibration method of a 3-D wearable ultrasound sensor probe 32 differs from the method as shown in FIG. 3 for a 2-D wearable ultrasound sensor 32 in that the manual repositioning in operation 73 to optimize the alignment of the wearable ultrasound sensor probe 32 with the artery 36 of the patient is replaced by an operation in which this repositioning is performed by electronic beam steering of the wearable 3-D ultrasound sensor probe 32.

The above described methods executed by the processor 38 of the patient monitor controller 30 may be realized by computer readable program instructions embodied on a computer readable storage medium which, when executed on the processor arrangement, cause the processor arrangement to implement any embodiment of the method. Any suitable computer readable storage medium may be used for this purpose, such as for example an optically readable medium such as a CD, DVD or Blu-Ray disc, a magnetically readable medium such as a hard disk, an electronic data storage device such as a memory stick or the like, and so on. The computer readable storage medium may be a medium that is accessible over a network such as the Internet, such that the computer readable program instructions may be accessed over the network. For example, the computer readable storage medium may be a network-attached storage device, a storage area network, cloud storage or the like. The computer readable storage medium may be an Internet-accessible service from which the computer readable program instructions may be obtained. In an embodiment, the patient monitor controller 30 is adapted to retrieve the computer readable program instructions from such a computer readable storage medium and to create a new computer readable storage medium by storing the retrieved computer readable program instructions in a data storage arrangement of the patient monitor controller 30, e.g. in a memory device or the like forming part of the patient monitor controller 30.

Figure 4:
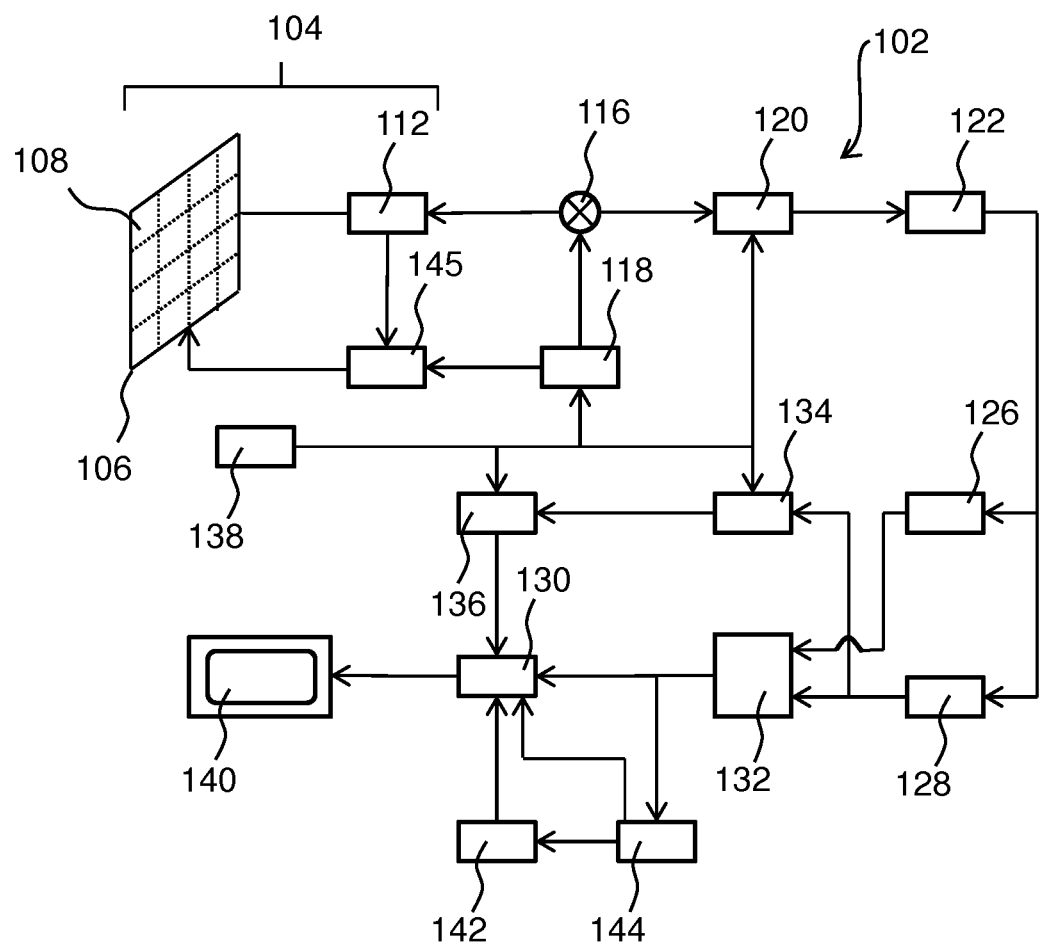
FIG. 4 shows an ultrasonic diagnostic imaging system with an array transducer probe in block diagram form, that may incorporate the invention.

For completeness, FIG. 4 shows an example of the components which may form a known ultrasound imaging system, which may be used in the system of the invention. A transducer array 106 of CMUT cells 108 as discussed above is for transmitting ultrasonic waves and receiving echo information. The transducer array 106 of the system 102 may generally be a one- or a two-dimensional array of transducer elements capable of scanning in a 2D plane or in three dimensions for 3D imaging. One such array may be used as each of the two or more probes of the invention.

The transducer array 106 is coupled to a micro-beamformer 112 which controls transmission and reception of signals by the CMUT array cells. Micro-beamformers are capable of at least partial beamforming of the signals received by groups or "patches" of transducer elements for instance as described in U.S. Pat. No. 5,997,479 (Savord et al.), U.S. Pat. No. 6,013,032 (Savord), and U.S. Pat. No. 6,623,432 (Powers et al.).

The micro-beamformer 112 is coupled by the probe cable, e.g. coaxial wire, to a transmit/receive (T/R) switch 116 which switches between transmission and reception modes and protects the main beamformer 120 from high energy transmit signals when a micro-beamformer is not present or used and the transducer array 106 is operated directly by the main system beamformer 120. The transmission of ultrasonic beams from the transducer array 106 under control of the micro-beamformer 112 is directed by a transducer controller 118 coupled to the micro-beamformer by the T/R switch 116 and the main system beamformer 120, which receives input from the user's operation of the user interface or control panel 138. One of the functions controlled by the transducer controller 118 is the direction in which beams are steered and focused. Beams may be steered straight ahead from (orthogonal to) the transducer array 106, or at different angles for a wider field of view.

The transducer controller 118 may be coupled to control a voltage source 145 for the transducer array. For instance, the voltage source 145 sets DC and AC bias voltage(s) that are applied to the CMUT cells of a CMUT array 106, e.g. to generate the ultrasonic RF pulses in transmission mode.

The partially beam-formed signals produced by the micro-beamformer 112 are forwarded to the main beamformer 120 where partially beam-formed signals from individual patches of transducer elements are combined into a fully beam-formed signal. For example, the main beamformer 120 may have 128 channels, each of which receives a partially beam-formed signal from a patch of dozens or hundreds of CMUT transducer cells 108. In this way the signals received by thousands of transducer elements of a transducer array 106 can contribute efficiently to a single beam-formed signal.

The beam-formed signals are coupled to a signal processor 122. The signal processor 122 can process the received echo signals in various ways, such as bandpass filtering, decimation, I and Q component separation, and harmonic signal separation which acts to separate linear and nonlinear signals so as to enable the identification of nonlinear (higher harmonics of the fundamental frequency) echo signals returned from tissue and microbubbles.

The signal processor 122 optionally may perform additional signal enhancement such as speckle reduction, signal compounding, and noise elimination. The bandpass filter in the signal processor 122 may be a tracking filter, with its passband sliding from a higher frequency band to a lower frequency band as echo signals are received from increasing depths, thereby rejecting the noise at higher frequencies from greater depths where these frequencies are devoid of anatomical information.

The processed signals are coupled to a B-mode processor 126 and to a Doppler processor 128. The B-mode processor 126 employs detection of an amplitude of the received ultrasound signal for the imaging of structures in the body such as the tissue of organs and vessels in the body. B-mode images of structure of the body may be formed in either the harmonic image mode or the fundamental image mode or a combination of both for instance as described in U.S. Pat. No. 6,283,919 (Roundhill et al.) and U.S. Pat. No. 6,458,083 (Jago et al.).

The Doppler processor 128 processes temporally distinct signals from tissue movement and blood flow for the detection of the motion of substances, such as the flow of blood cells in the image field. The Doppler processor typically includes a wall filter with parameters which may be set to pass and/or reject echoes returned from selected types of materials in the body. For instance, the wall filter can be set to have a passband characteristic which passes signal of relatively low amplitude from higher velocity materials while rejecting relatively strong signals from lower or zero velocity material.

This passband characteristic will pass signals from flowing blood while rejecting signals from nearby stationary or slowing moving objects such as the wall of the heart. An inverse characteristic would pass signals from moving tissue of the heart while rejecting blood flow signals for what is referred to as tissue Doppler imaging, detecting and depicting the motion of tissue. The Doppler processor receives and processes a sequence of temporally discrete echo signals from different points in an image field, the sequence of echoes from a particular point referred to as an ensemble. An ensemble of echoes received in rapid succession over a relatively short interval can be used to estimate the Doppler shift frequency of flowing blood, with the correspondence of the Doppler frequency to velocity indicating the blood flow velocity. An ensemble of echoes received over a longer period of time is used to estimate the velocity of slower flowing blood or slowly moving tissue.

The structural and motion signals produced by the B-mode (and Doppler) processor(s) are coupled to a scan converter 132 and a multiplanar reformatter 144. The scan converter 132 arranges the echo signals in the spatial relationship from which they were received in a desired image format. For instance, the scan converter may arrange the echo signal into a two dimensional (2D) sector-shaped format, or a pyramidal three dimensional (3D) image.

The scan converter can overlay a B-mode structural image with colors corresponding to motion at points in the image field with their Doppler-estimated velocities to produce a color Doppler image which depicts the motion of tissue and blood flow in the image field. The multiplanar reformatter 144 will convert echoes which are received from points in a common plane in a volumetric region of the body into an ultrasonic image of that plane, for instance as described in U.S. Pat. No. 6,443,896 (Detmer). A volume renderer 142 converts the echo signals of a 3D data set into a projected 3D image as viewed from a given reference point as described in U.S. Pat. No. 6,530,885 (Entrekin et al.). The 2D or 3D images are coupled from the scan converter 132, multiplanar reformatter 144, and volume renderer 142 to an image processor 130 for further enhancement, buffering and temporary storage for display on an image display 140. In addition to being used for imaging, the blood flow values produced by the Doppler processor 128 and tissue structure information produced by the B-mode processor 126 are coupled to a quantification processor 134. The quantification processor produces measures of different flow conditions such as the volume rate of blood flow as well as structural measurements such as the sizes of organs and gestational age. The quantification processor may receive input from the user control panel 138, such as the point in the anatomy of an image where a measurement is to be made.

Output data from the quantification processor is coupled to a graphics processor 136 for the reproduction of measurement graphics and values with the image on the display 140. The graphics processor 136 can also generate graphic overlays for display with the ultrasound images. These graphic overlays can contain standard identifying information such as patient name, date and time of the image, imaging parameters, and the like. For these purposes the graphics processor receives input from the user interface 138, such as patient name.

The user interface is also coupled to the transmit controller 118 to control the generation of ultrasound signals from the transducer array 106 and hence the images produced by the transducer array and the ultrasound system. The user interface is also coupled to the multiplanar reformatter 144 for selection and control of the planes of multiple multiplanar reformatted (MPR) images which may be used to perform quantified measures in the image field of the MPR images.

As will be understood by the skilled person, the above embodiment of an ultrasonic diagnostic imaging system is intended to give a non-limiting example of such an ultrasonic diagnostic imaging system. The skilled person will immediately realize that several variations in the architecture of the ultrasonic diagnostic imaging system are feasible without departing from the teachings of the present invention. For instance, as also indicated in the above embodiment, the micro-beamformer 112 may be omitted, the ultrasound probe 104 may not have 3D imaging capabilities and so on.

A preferred embodiment of the invention will now be described with reference to FIGS. 5 to 7. It will be understood that this may be incorporated in a system of the type described above with reference to FIGS. 2 and 3 or FIG. 4, by using two, or more than two, ultrasonic probes, and placing them at separate locations on the body of the patient to detect arterial flow and preferably also arterial diameter.

Two or more low-cost ultrasound patches, illustrated as probe 32 of FIG. 2, are each placed on the skin above a major artery (e.g. carotid and brachial), to detect the onset of centralization at an immediate stage, by monitoring blood flow redistribution. Typically, at rest, the brachial flow is four times lower than the carotid flow. Flow in radial arteries and femoral arteries has its own typical ratio to the carotid flow. This ratio forms a patient- and cardiac output-independent measure of blood volume distribution. Changes in the ratio of, e.g., (highest, lowest, or mean) brachial volumetric flow (or flow velocity) over the (highest, lowest, or mean) carotid volumetric flow (or flow velocity), between the sensor sites indicate volume redistribution and centralization in critical illness and, for example, limb ischemia in vascular surgery. This low-cost, easy-to-implement solution allows timely intervention for haemodynamic insufficiency and provides support for optimal fluid management in peri-operative patients.

Figure 5:
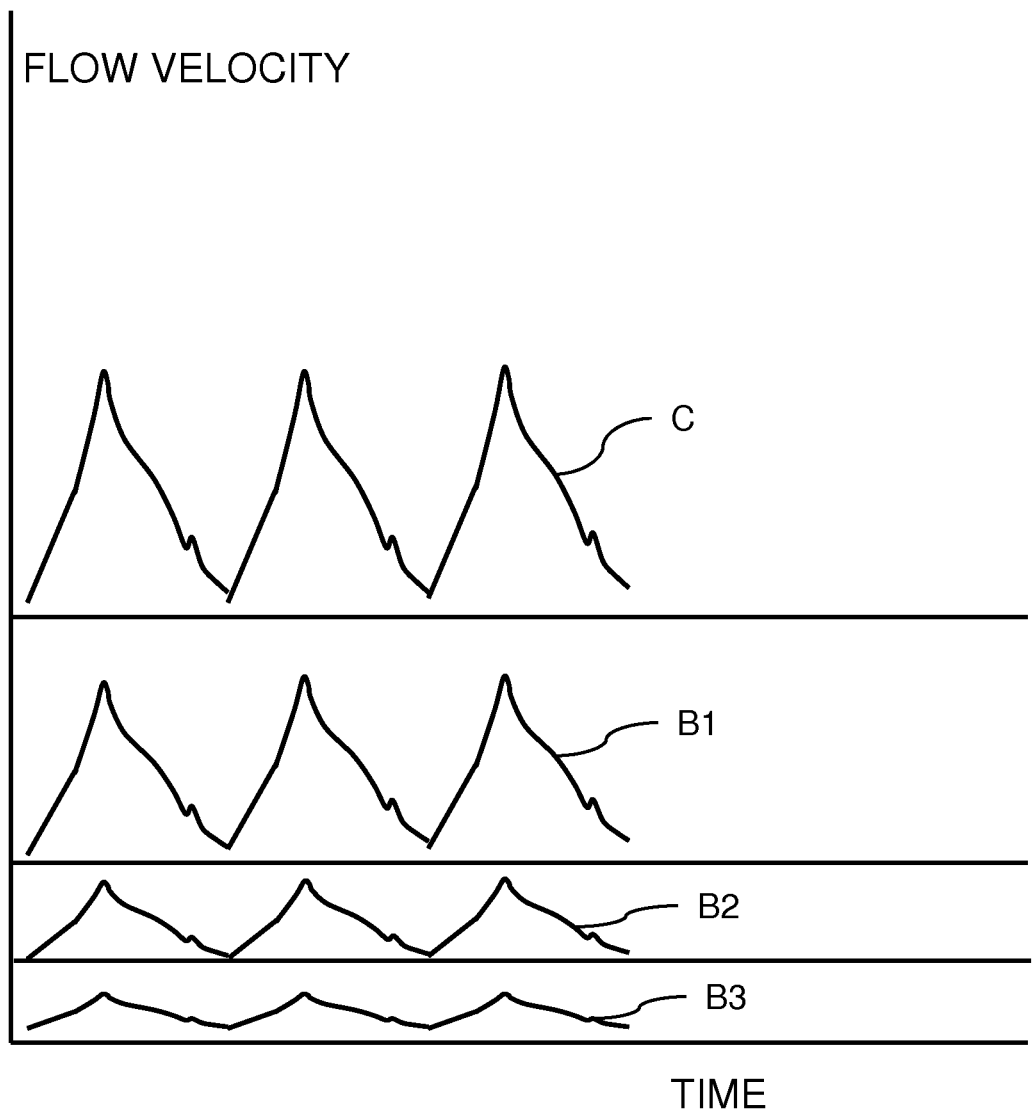
FIG. 5 is a graph of flow velocity against time as measured at the carotid and brachial arteries.

A simple example of how the signals can be analysed to detect volume (re)distribution is given in FIG. 5. Carotid flow velocity C shown over three heart beats is compared with brachial flow velocity and the trace B1 where the numerical ratio is less than 2 (here about 1.2) is indicative of hypervolemia (centralization), the trace B2 where the ratio is 4 is indicative of normovolemia (no centralization), and the trace B3 where the ratio is greater than 8 is indicative of hypovolemia (centralization). The ratio in peak velocities is used, in this example, as a surrogate for the rate in 'stroke volumes' i.e. the volume of blood flowing through the artery in each heartbeat. An alternative would be to integrate the Doppler velocity over the period of the heartbeat, and to obtain the corresponding "distance" ratios. Rather than that, the actual volume that flows through the artery per heartbeat and per minute could be obtained by integrating the Doppler velocity measurement (over the relevant period) and multiplying this by the arterial diameter, to give volumetric flow rate; multiplying this rate by the duration of a heart beat gives the 'stroke volume'. The arterial diameter can either be found in calibration tables taking gender, age, height and weight into account, measured with a spot check a priori and entered into the monitor controller 30, or can be measured, as described above, with an ultrasound sensor probe 32 for example by imaging. Pulse wave Doppler imaging can be used for this purpose. The same probe can be used as is used for Doppler velocity measurement.

Figure 6:
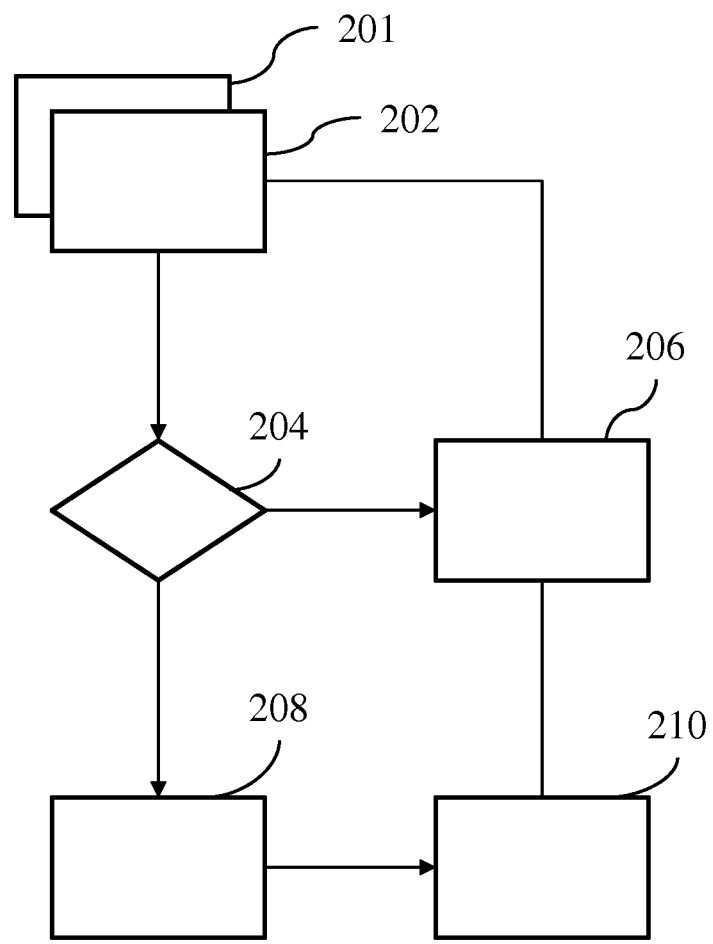
FIG. 6 is a block diagram showing a method embodying the invention of detecting blood volume distribution change.

FIG. 6 depicts schematically how the flow signals are input to an algorithm, run by a program in the processor 38 of the controller 30, that derives the blood volume (re) distribution. Blood flow signals, for example the Doppler flow velocity signals shown in FIG. 5, are obtained in steps 201 and 202 from the carotid and brachial (or other) arteries. The volume estimate at each location is calculated by integrating the Doppler velocity over each cycle, such as one heartbeat, and multiplying by an estimate of the arterial diameter as described above. The ratio (e.g. Vbrachial/Vcarotid) of these volume estimates is then determined. In step 204, the program determines whether the ratio has been obtained for the first time in the current operation of the monitoring system since initialization. The first ratio in a time sequence of estimates is normally taken to be the reference ratio. If the first ratio is considered to be within the expected range (e.g. Vbrachial/Vcarotid is 3-5), then the ratio is set or reset in step 208 as the reference value. Consecutive ratios are compared to the reference value and stored in step 206 as the updated ratio. When the new ratio differs significantly from the reference (e.g. by 10% or more), a notification may be provided in step 210 as this indicates a change in blood volume distribution (an increase indicates centralization and a decrease indicates recovery or fluid overload). Furthermore, if the first ratio is far outside the expected range (e.g. Vbrachial/Vcarotid>6), then in step 210 a notification may be provided, as this may indicate centralization.

With reference to FIG. 5 and the ranges indicative of hypovolemia etc., the reference value for the ratio of flow was taken to be 4; if that became more than 8 hypovolemia was indicated, and if it became less than 2 hypervolemia was indicated. This simple algorithm can be adapted by setting the ratio reference value in step 208, and using as upper and lower thresholds a predetermined percentage above and below this reference.

The output from step 210 is processed as one of the additional inputs 43 to the controller 30 of FIG. 2, for example, to generate a haemodynamic display in the monitor 20 and optionally an alarm from unit 44. This indicates to the caregiver the onset of hypovolemia or hypervolemia causing centralization of the blood volume. This indication may be compared, as described above, with other monitored signs. This may enable the distinction to be made between hypovolemia and hypervolemia.

One outcome may be for the controller 30 automatically to signal a fluid management unit 46 such as a bedside controller to increase or decrease the rate of intravenous saline or plasma flow to the patient.

Figure 7:
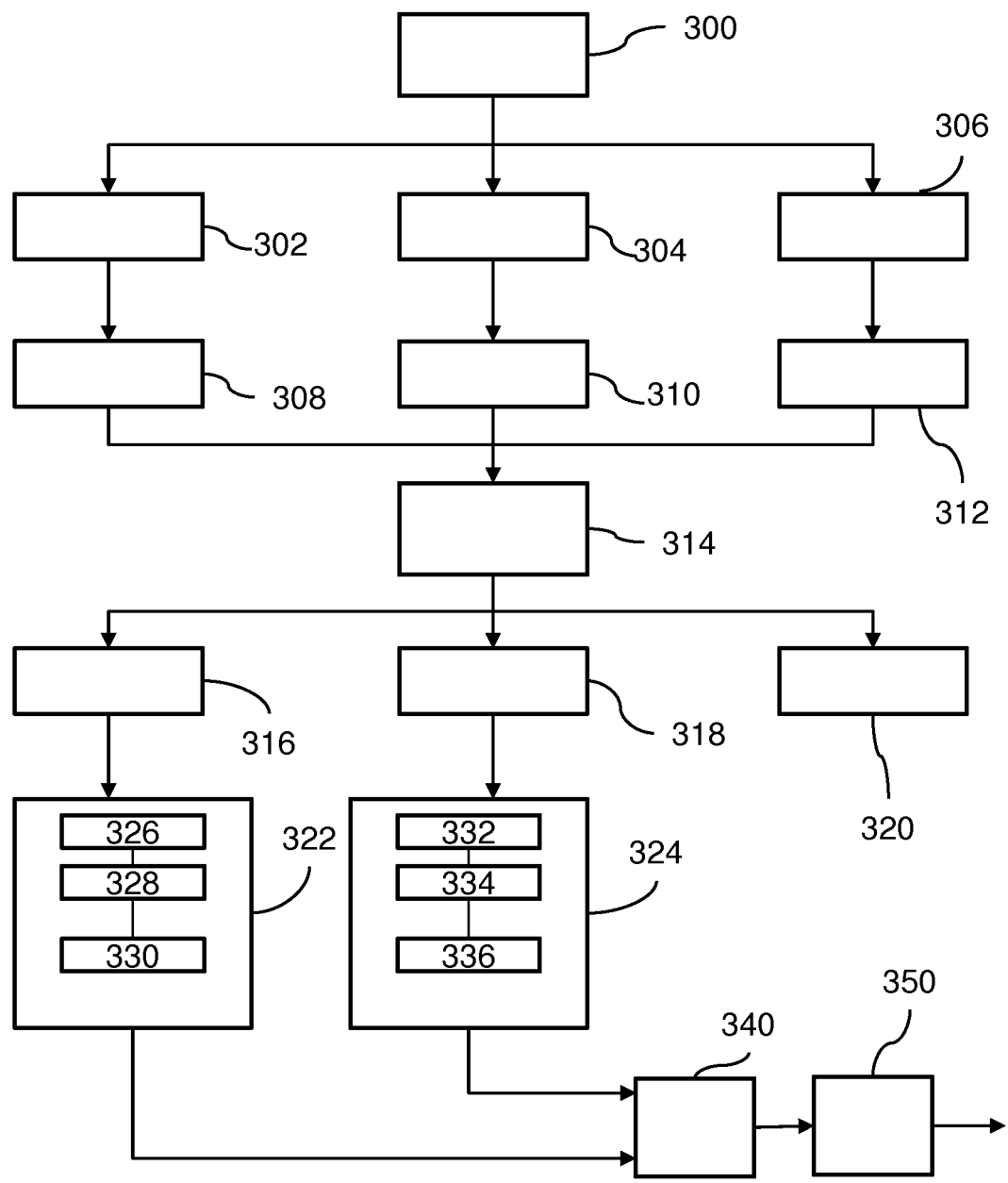
FIG. 7 is a block diagram showing the use of three probes with the method of FIG. 6 in more detail.

In greater detail, the program traverses through the steps as shown in FIG. 7, where a probe configuration is determined at initialization to set the number of probes and their locations. Consecutively, each probe is configured according to these positions; specifically the size of the scanning area (or volume) is set and the probe's pulse characteristics such as frequency, power and number of pulses.

To quantify the velocity in a certain artery, PW (Pulsed Wave) Doppler is used to set the ROI and the area of measurement. Using CW (Continuous Wave) Doppler will give an average of all flow in the US beam (not limited to a fixed depth). So both modes can be used advantageously.

In this example, three probes (patches) A, B and C similar to probe 32 are provided and are attached to the body over the carotid, brachial and femoral arteries respectively. The probes A, B and C are set up in steps 302, 304 and 306 and then in steps 308, 310 and 312 each probe performs a Doppler velocity measurement in the configured measurement area over a period that typically spans a heart cycle. From these measurements, a region of interest ROI and quality estimate of the detected flow follow. The ROI represents the estimated location of an artery through which flow is measured. The quality estimate is used to indicate if a reliable flow measurement can be performed.

In step 314, the probe configurations are all updated. For each probe, a possible probe configuration is determined to measure flow continuously. With these settings, in steps 316 and 318 the probes A and B are reconfigured (i.e. setting the probe's steering angle and driving scheme for focus and frequency) for optimal continuous flow measurement. This entails measuring the velocity in a specific region, updating the ROI to track possible movement of the artery (or the probe) and updating the phase estimate in the heart cycle. In case the quality of a scan was insufficient during initialization, following step 314 a probe, in this example probe C, can be temporarily disabled for continuous flow measurement, in step 320. For each enabled probe, the measurement parameters are updated and the scans are then performed in blocks 322 and 324 respectively, simultaneously. In block 322, the region ROI is updated in step 326 and the scan period is updated in step 328. In block 324, the region ROI is updated in step 332 and the scan period is updated in step 334. Doppler scanning is performed in steps 330 and 336. The flow data from these scans are processed in step 340 to determine the heart cycle period, and in step 350 to determine the (averaged) ratio over each heart cycle. In this example, the data from only the probes A and B are processed to derive the ratio.

This routine shown in FIG. 7 may be repeated regularly, for example at 15 minute intervals.

When using two ultrasound patches for flow monitoring in two major arteries, such as the carotid and the brachial or the brachial and the radial arteries, the obtained flow signals can also be used to provide an estimate of cardiac output. This may be provided by the controller as an additional output for display on the monitor 20. In principle, this is also possible using only one ultrasound patch. When using only one patch, it should be placed on an artery through which the perfusion is highly dependent on the cardiac output. The brachial artery, or arteries downstream of that such as the radial artery, are good options. Using two patches, however, not only doubles the accuracy, but it also extends the dynamic range for cardiac output measurement when the second (more peripheral) patch is placed on an artery for which the perfusion is more stable under a wider cardiac output range. The dynamic range of the system (i.e. the cardiac output range it can reliably measure) then increases accordingly, because measurements from both patches or either patch can be used. As an example, and with further reference to FIG. 1, when cardiac output gradually decreases, the perfusion in the radial artery will lower first, followed by lowering of the perfusion in the brachial artery. As such, the radial artery perfusion will hit a minimum quite quickly when cardiac output decreases (i.e. there is no longer any correlation between radial perfusion and cardiac output), while the perfusion of the brachial artery still exhibits a dependency on cardiac output. Adding another patch, for example to the carotid artery, increases the dynamic range of the system to very high and very low cardiac outputs (ie the range outside the autoregulation range of the brain).

Figure 8:
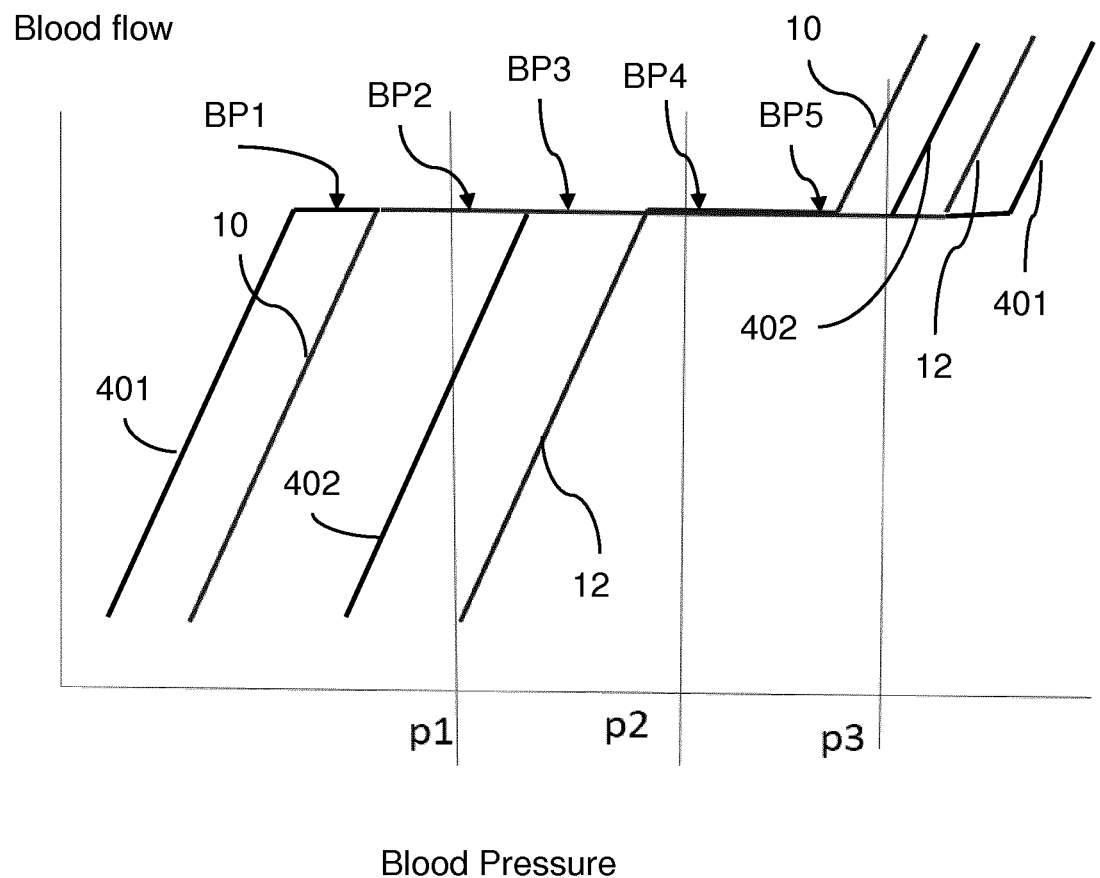
FIG. 8 is a graph of blood pressure and blood flow for multiple different parts of the body.

Although the use of probes at only two locations is described above, using multiple probes on multiple arteries, one increases either the range or the resolution. For example, as shown in FIG. 8, blood flow is measured at the heart, line 401, and the kidney (renal artery), line 402, in addition to the carotid artery, line 10 and the brachial artery, line 12 which are the same as lines 10 and 12 in FIG. 1. Starting with probes on arteries that have flow properties that behave like lines 401 and 12 in FIG. 8, the pressure range over which changes can be measured is large, but the resolution/accuracy is low. Adding a probe on an artery with flow properties that behave like the lines 10 and 402, between the extremes, would improve the accuracy of the measurements. Vice versa, when starting with probes where the characteristics are like lines 401 and 10, adding a probe with a characteristic like line 12 would increase the range. Actual blood pressure values can be derived from the flow measurements, and multiple flow measurements can be taken simultaneously at specific locations where the relative width of the constant pressure ranges is known as demonstrated in FIG. 8. The graph shows that when flow is measured at multiple locations, multiple pressure values, BP1 compared with BP2 and with BP3, can be discriminated based on the ratios between flows, using the lines 401, 10 and 402, according to a simple algorithm. On the other hand, for other pressures (e.g. BP4 vs BP5) these differences in pressure cannot be discriminated. Changes in flow give input on centralization.

The change in diameter of the inferior vena cava (IVC) for example may give additional information on the fluid status of the patient, and could be used together with the monitoring of the changes described according to the invention.

An aspect of this disclosure is the diagnostic method of taking and using blood flow measurements at two different locations on the body. This method of detecting the onset of hypovolemia (and/or hypervolemia) comprises taking Doppler ultrasound measurements of arterial blood flow velocity in at least two different locations of a subject, preferably simultaneously or in quick succession, to obtain a measure of the blood flow at each location, monitoring changes in a predetermined function of the blood flow measures, and providing an output indicative of the monitored changes. The output preferably includes information on whether the monitored changes indicate hypovolemia or hypervolemia.

As discussed above, embodiments make use of a controller. The controller can be implemented in numerous ways, with software and/or hardware, to perform the various functions required. A processor is one example of a controller which employs one or more microprocessors that may be programmed using software (e.g., microcode) to perform the required functions. A controller may however be implemented with or without employing a processor, and also may be implemented as a combination of dedicated hardware to perform some functions and a processor (e.g., one or more programmed microprocessors and associated circuitry) to perform other functions.

Although the controller is separate from the probes in the embodiments described, its functionality could instead be integrated into one or more of the probes.

The communications between the probes and the controller are described as wireless in the embodiments, but they could be wired, by having cables between the probes or between the probes and the controller, or both. In this case, the probes could be powered from an external source such as the controller, and need not then have internal power sources. However, wired connections could make the usage of the probes more difficult and painful.

The probes are conveniently mounted as patches on the surface of the skin. However, the invention could use more invasive techniques, such as probes within the subject's tissue.

Examples of controller components that may be employed in various embodiments of the present disclosure include, but are not limited to, conventional microprocessors, application specific integrated circuits (ASICs), and field-programmable gate arrays (FPGAs).

In various implementations, a processor or controller may be associated with one or more storage media such as volatile and non-volatile computer memory such as RAM, PROM, EPROM, and EEPROM. The storage media may be encoded with one or more programs that, when executed on one or more processors and/or controllers, perform the required functions. Various storage media may be fixed within a processor or controller or may be transportable, such that the one or more programs stored thereon can be loaded into a processor or controller.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. A system for monitoring blood distribution in a subject, the system comprising:
 a processor adapted to:
  receive Doppler ultrasound data representing a first arterial blood flow value at a first location and a second arterial blood flow value at a second location of the subject;
  perform a first comparison of the first arterial blood flow value and the second arterial blood flow value, wherein the first comparison comprises calculation of a ratio between the first arterial blood flow value and the second arterial blood flow value, wherein the ratio is associated with the blood distribution in the subject;
  perform a second comparison of the ratio to a first threshold associated with hypovolemia and to a second threshold associated with hypervolemia;
  detect the hypovolemia, when the ratio is greater than the first threshold;
  detect the hypervolemia when the ratio is less than the second threshold; and
  generate an output indicative of the hypovolemia when the ratio is greater than the first threshold and indicative of the hypervolemia when the ratio is less than the second threshold.

2. The system according to claim 1, wherein the first arterial blood flow value comprises an arterial blood flow velocity integrated over a period of a heart beat of the subject.

3. The system according to claim 1,
 wherein the processor is responsive to a measure of a diameter of the artery at the first location, and
 wherein a volumetric rate of flow of the blood is based on the diameter and a flow velocity.

4. The system according to claim 3, wherein the first arterial blood flow value comprises the volumetric flow rate integrated over a period of a heart beat of the subject.

5. The system according to claim 1, comprising a fluid management system configured to:
 provide fluid to the subject; and
 control a provision of the fluid responsive to the output indicative of the hypovolemia or the hypervolemia.

6. The system according to claim 1, wherein the processor is configured to generate an output indicative of a cardiac output of the subject, based on blood perfusion in at least the first location obtained by integrating over time a blood flow velocity at the first location multiplied by a diameter of the artery at the first location.

7. The system according to claim 1, comprising at least two Doppler ultrasound probes configured to measure an arterial blood flow velocity in the at least the first location and the second location of the subject and to provide the Doppler ultrasound data to the processor.

8. The system according to claim 1, comprising at least one Doppler ultrasound probe configured to image an artery at one of the the first location or the second location of the subject to provide to the processor a diameter of the artery.

9. The system according to claim 8, comprising a subject monitor configured to display the output indicative of the hypovolemia or the hypervolemia.

10. The system according to claim 1,
 wherein the Doppler ultrasound data represents a plurality of first arterial blood flow values at the first location and a plurality of second arterial blood flow values at the second location, and
 wherein the processor is further adapted to monitor the ratio over time based on the plurality of the first arterial blood flow values and the plurality of the second arterial blood flow values.

11. The system according to claim 10, wherein the processor is further adapted to:
 detect, based on the monitoring of the ratio over time, an onset of the hypovolemia or an onset of the hypervolemia.

12. The system according to claim 10, wherein the ratio comprises a mean of the plurality of first arterial blood flow values over a mean of the plurality of second arterial blood flow values.

13. The system according to claim 1, comprising a speaker configured to sound an alarm corresponding to the output indicative of the hypovolemia or the hypervolemia.

14. A method of monitoring blood distribution in a subject, comprising:
  receiving Doppler ultrasound data representing a first arterial blood flow value at a first location and a second arterial blood flow value at a second location of the subject;
  performing a first comparison of the first arterial blood flow value and the second arterial blood flow value, wherein the first comparison comprises calculation of a ratio between the first arterial blood flow value and the second arterial blood flow value, wherein the ratio is associated with the blood distribution in the subject;
  performing a second comparison of the ratio to a first threshold associated with hypovolemia and to a second threshold associated with hypervolemia;
  detecting the hypovolemia when the ratio is greater than the first threshold;
  detecting the hypervolemia when the ratio is less than the second threshold; and
  generating an output indicative of the hypovolemia when the ratio is greater than the first threshold and indicative of the hypervolemia when the ratio is less than the second threshold.

15. The method according to claim 14, wherein the first location and second location of the subject are at substantially different distances from a heart.

16. The method of claim 15,
  wherein the first location comprises a carotid artery, and
  wherein the second location comprises a brachial, femoral or radial artery.

17. The method of claim 14, comprising at least one of:
  displaying the output indicative of the hypovolemia or the hypervolemia on a subject monitor; or
  sounding an alarm corresponding to the output indicative of the hypovolemia or the hypervolemia with a speaker.

18. A non-transitory computer readable medium comprising a plurality of instructions stored thereon, wherein, when executed by a processor, the plurality of instructions is configured to cause the processor to:
  receive Doppler ultrasound data representing a first arterial blood flow value at a first location and a second arterial blood flow value at a second location of a subject;
  perform a first comparison of the first arterial blood flow value and the second arterial blood flow value, wherein the first comparison comprises calculation of a ratio between the first arterial blood flow value and the second arterial blood flow value, wherein the ratio is associated with a blood distribution in the subject;
  perform a second comparison of the ratio to a first threshold associated with hypovolemia and to a second threshold associated with hypervolemia;
  detect the hypovolemia when the ratio is greater than the first threshold;
  detect the hypervolemia in the subject when the ratio is less than the second threshold; and
  generate an output indicative of the hypovolemia when the ratio is greater than the first threshold and indicative of the hypervolemia when the ratio is less than the second threshold.

* * * * *